United States Patent [19]

Plattier et al.

[11] 3,956,196

[45] May 11, 1976

[54] NOVEL ODORIFEROUS COMPOSITIONS CONTAINING HETEROCYCLIC 4,5-DECAMETHYLENE COMPOUNDS

[75] Inventors: Marcel Plattier, Antibes; Bernard Shimizu; Paul José Teisseire, both of Grasse, all of France

[73] Assignee: Societe Anonyme Roure Bertrand Dupont, Paris, France

[22] Filed: Sept. 16, 1974

[21] Appl. No.: 506,213

[30] Foreign Application Priority Data

Sept. 28, 1973 Switzerland ...................... 13977/73

[52] U.S. Cl. ............................................. 252/522

[51] Int. Cl.[2] ........................ A61K 7/46; C11B 9/00

[58] Field of Search ..................................... 252/522

[56] References Cited

UNITED STATES PATENTS 3,773,525 11/1973 Pittet et al. ......................... 252/522

FOREIGN PATENTS OR APPLICATIONS 1,114,497 7/1959 Germany

OTHER PUBLICATIONS

Wasserman et al., JACS 90, pp. 2440–2441, (1968).

*Primary Examiner*—C. Davis

*Attorney, Agent, or Firm*—Wallenstein, Spangenberg, Hattis & Strampel

[57] ABSTRACT

Odoriferous compositions containing heterocyclic 4,5-decamethylene compounds of the formulae I and/or II

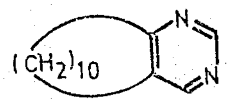

I

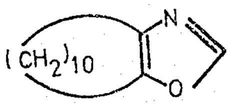

II are disclosed.

3 Claims, No Drawings

NOVEL ODORIFEROUS COMPOSITIONS CONTAINING HETEROCYCLIC 4,5-DECAMETHYLENE COMPOUNDS

The present invention is concerned with odorant compositions containing heterocyclic 4,5-decamethylene compounds.

The heterocyclic 4,5-decamethylene compounds of the formulae

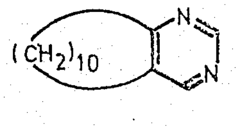

I

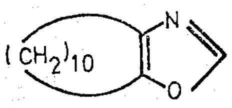

II are known per se: the compound of formula I for example, from the German Pat. No. 1,114,497 and the compound of formula II from J.A.C.S. (1968) 90, 2440. It has now surprisingly been found in accordance with the present invention that these compounds are distinguished by special odorant properties. Thus the 4,5-decamethylene-pyrimidine of the formula I has an aroma with a musk-like note of the macrocyclic type, as well as an amber note with an underlying woody side note, which appears and develops in the course of evaporation of the substance giving the product a particular originality. The 4,5-decamethyleneoxazole of the formula II also has a musk-like odour with an amber note. This compound also displays tobacco notes.

The present invention accordingly concerns the use of the compounds I and/or II as odorants in perfumery, for example for the manufacture of odorant compositions or for modifying the fragrance of such, such as perfumes, or for perfuming products such as cosmetics, soaps, washing agents etc. Further objects of the invention are odorant compositions with a content of a compound of the formula I and/or II.

Compound II can be manufactured as described in the said literature [J.A.C.S. (1968) 90, 2440]. However, it can also be obtained by allowing ammonium formate to react with 2-bromo-cyclododecanone in the presence of formic acid.

The amounts of compound I or II for use in accordance with the invention as odorants can vary within wide limits. In the manufacture of odorant concentrates, the amount comes, for example, to approximately 1 to approximately 50 wt.%. For the manufacture of perfumes, the compounds can be employed in amounts of a few parts per thousand to more than 40% by weight.

The use of the compounds according to the invention is illustrated by the following Example.

EXAMPLE

| Odorant composition (Musk oil): | Parts by weight |
|---|---|
| Geranium oil Bourbon | 20 |
| Sandalwood oil (East Indian) | 300 |
| Mixture of 4-(1-ethoxyvinyl)-3,3,5,5-tetramethylcyclohexanone and 1-ethoxy-4-(1-ethoxyvinyl)-3,3,5,5-cyclo-1-hexene | 10 |
| p-Hydroxyphenylbutanone (1% in dipropyleneglycol) | 10 |
| Coumarin | 10 |
| Peru Balsam oil | 30 |
| Tonkin musk (20%) | 10 |
| Dipropyleneglycol | 210 |
| 4,5-Decamethylene-pyrimidine | 400 |
| | 1000 |

What is claimed is:

1. An odorant composition which contains a carrier and, in addition, as an odorant, a herterocyclic 4,5-decamethylene derivative having the formula I and/or II

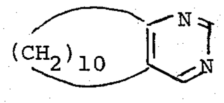

I

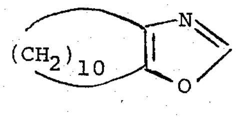

II

2. An odorant composition according to claim 1, in the form of a concentrate, containing from approximately 1 to approximately 50 wt. % of said derivatives having the formula I and/or II.

3. An odorant composition according to claim 1, in the form of a perfume, containing up to about 40% by weight of said derivatives having the formula I and/or II.

* * * * *